(12) United States Patent
Tsubokura et al.

(10) Patent No.: US 10,214,419 B2
(45) Date of Patent: Feb. 26, 2019

(54) GRANULES OR POWDER OF DISULFONYLAMIDE SALT AND METHOD FOR PRODUCING SAME

(71) Applicant: Nippon Soda Co., Ltd., Chiyoda-ku, Tokyo (JP)

(72) Inventors: Shiro Tsubokura, Takaoka (JP); Yasuyuki Aiura, Myoko (JP)

(73) Assignee: Nippon Soda Co., Ltd., Tokyo (JP)

( * ) Notice: Subject to any disclaimer, the term of this patent is extended or adjusted under 35 U.S.C. 154(b) by 128 days.

(21) Appl. No.: 15/035,011

(22) PCT Filed: Oct. 31, 2014

(86) PCT No.: PCT/JP2014/079054
§ 371 (c)(1),
(2) Date: May 6, 2016

(87) PCT Pub. No.: WO2015/072353
PCT Pub. Date: May 21, 2015

(65) Prior Publication Data
US 2016/0289074 A1    Oct. 6, 2016

(30) Foreign Application Priority Data

Nov. 18, 2013 (JP) .................... 2013-237991

(51) Int. Cl.
| | | |
|---|---|---|
| C01B 21/086 | (2006.01) | |
| C07C 311/48 | (2006.01) | |
| H01M 10/0568 | (2010.01) | |
| C01B 21/093 | (2006.01) | |
| H01M 10/0563 | (2010.01) | |

(52) U.S. Cl.
CPC .......... *C01B 21/086* (2013.01); *C01B 21/093* (2013.01); *C07C 311/48* (2013.01); *H01M 10/0568* (2013.01); *C01P 2004/61* (2013.01); *C01P 2006/40* (2013.01); *H01M 10/0563* (2013.01)

(58) Field of Classification Search
None
See application file for complete search history.

(56) References Cited

U.S. PATENT DOCUMENTS

| | | | |
|---|---|---|---|
| 4,876,341 A | 10/1989 | Schütz et al. | |
| 5,874,616 A | 2/1999 | Howells et al. | |
| 5,916,475 A | 6/1999 | Michot et al. | |
| 6,365,301 B1 | 4/2002 | Michot et al. | |
| 2001/0025943 A1 | 10/2001 | Michot et al. | |
| 2010/0137609 A1 | 6/2010 | Iwaya | |
| 2012/0189793 A1 | 7/2012 | Tsuneizumi et al. | |
| 2013/0068991 A1 | 3/2013 | Sato et al. | |
| 2013/0323154 A1 | 12/2013 | Tsubokura et al. | |
| 2013/0323155 A1 | 12/2013 | Tsubokura et al. | |
| 2013/0331609 A1 | 12/2013 | Tsubokura et al. | |
| 2014/0142338 A1* | 5/2014 | Johnson ................ C07C 209/68 564/296 |
| 2014/0241973 A1 | 8/2014 | Fukunaga et al. | |

FOREIGN PATENT DOCUMENTS

| | | |
|---|---|---|
| CN | 101778835 A | 7/2010 |
| CN | 102786451 A | 11/2012 |
| EP | 2662332 A1 | 11/2013 |
| JP | 2001-527505 A | 12/2001 |
| JP | 2004-269491 A | 9/2004 |
| JP | 2006-210331 A | 8/2006 |
| JP | 2007-182410 A | 7/2007 |
| JP | 2011-116895 A | 6/2011 |
| JP | 2013-087019 A | 5/2013 |
| JP | 2013-089365 A | 5/2013 |
| JP | 2014-162680 A | 9/2014 |
| JP | 2014-201453 A | 10/2014 |
| WO | WO 2011/149095 A1 | 12/2011 |
| WO | WO 2012/108284 A1 | 8/2012 |
| WO | WO 2012/117961 A1 | 9/2012 |
| WO | WO 2012/118063 A1 | 9/2012 |

(Continued)

OTHER PUBLICATIONS

Supplementary Partial European Search Report dated Feb. 9, 2017, in EP 14861940.6.

(Continued)

*Primary Examiner* — Wayne A Langel
(74) *Attorney, Agent, or Firm* — Foley & Lardner LLP

(57) ABSTRACT

Granules or powders consisting of a compound of formula [I], in which a modal diameter is 80 μm or less, a median diameter is 45 μm or less, and/or, a ratio of (modal diameter)/(median diameter) is 1.7 or less, are preferably used for an electrolyte or the like.

[Chemical formula 1]

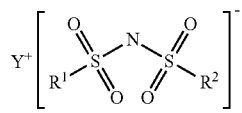

[I]

In formula [I], $R^1$ and $R^2$ each independently represents a fluoroalkyl group having 1 to 6 carbon atoms, or a fluorine atom, and $Y^+$ represents an alkali metal cation or an ammonium cation.

13 Claims, No Drawings

(56) References Cited

FOREIGN PATENT DOCUMENTS

| WO | WO 2013/172190 A1 | 11/2013 |
| WO | WO 2014/148258 A1 | 9/2014 |

OTHER PUBLICATIONS

Abouimrane et al., "Liquid electrolyte based on lithium bis-fluorosulfonyl imide salt: Aluminum corrosion studies and lithium ion battery investigations," Journal of Power Sources, Apr. 1, 2009, 189(1):693-696.

Office Action dated Jul. 18, 2017, in JP 2016-183498, with English translation.

Office Action dated Aug. 8, 2017, in JP 2016-183498, with English translation.

Kinose et al., "Development of Lithium Sulfide for Solid Electrolyte," 2007, home page of Nippon Chemical Industrial Co., Ltd., with full English translation, https://www.nippon-chem.co.jp/dcms_media/other/cre2007-6.pdf.

Office Action dated Jul. 8, 2016, in SG Application No. 11201601554S.

International Search Report dated Feb. 3, 2015, in PCT/JP2014/079054.

Notification of Third Party Observation submitted Mar. 11, 2016, against PCT/JP2014/079054.

Office Action dated Jul. 23, 2015, in Taiwan Application No. 103138126.

Beran et al., "A New Method of Preparation of Imido-bis(sulfuric acid) Dihalogenide, (F,Cl), and the Potassium Salt of Imido-bis(sulfuric acid) Difluoride," Z. Anorg. Allg. Chem., 2005, 631:55-59.

Horiba Scientific, "A Guidebook to Particle Size Analysis," Horiba Instruments, Inc., 2012, 32 pages.

Matsuda et al., "Effect of Imide Salt Purity in Electrolytes on Charge-Discharge Performance of Negative Electrodes for Lithium Secondary Batteries," Proceedings of the 68th Conference of the Electrochemical Society of Japan, Mar. 25, 2001, p. 232, 2L18, with partial English translation.

Yokota et al,. "Equation of Purity for Crystals Produced from a CMSMPR Crystallizer," Chem. Eng. Comm., 2003, 190:533-539.

Office Action dated Dec. 1, 2016, in CN 201480056583.8, with English translation.

Notification (Information Statement) dated Dec. 5, 2017, in JP 2016-183498, with English translation.

Office Action dated Dec. 22, 2017, in JP 2016-183498, with English translation.

\* cited by examiner

GRANULES OR POWDER OF DISULFONYLAMIDE SALT AND METHOD FOR PRODUCING SAME

TECHNICAL FIELD

The present invention relates to granules or powders of a di(sulfonylamide) salt, and a method for producing the same. In more detail, the present invention relates to granules or powders of a di(sulfonylamide) salt, such as a di(sulfonylamide) alkali metal salt, or a di(sulfonylamide) ammonium salt, suitable for an electrolyte or the like, and to a method for producing the same.

The present invention is a National Stage application of PCT/JP2014/073054, filed Oct. 31, 2014, which claims priority on the basis of Japanese Patent Application No. 2013-237991 filed in Japan on Nov. 18, 2013, the contents of which are incorporated herein by reference.

BACKGROUND OF THE INVENTION

Di(sulfonylamide) salts such as bis(fluorosulfonyl)amide alkali metal salts ($M^+[(FSO_2)_2N]^-$) are useful as ionic conducting materials or electrolytes or additives available in secondary cells (Patent Document 1, Patent Document 2). In the case where the compounds are used as electrolytes, it has been reported that the smaller amount of impurities, such as water, ash, $SO_4^{2-}$, or residual solvents, in the compounds, is more preferable (Non-Patent Document 1, Patent Document 3).

Various methods are known as a method for producing a bis(fluorosulfonyl)amide salt. For example, according to Non-Patent Document 2, a bis(fluorosulfonyl)amide potassium salt is obtained by reacting a compound with potassium fluoride, the compound being obtained by reacting sulfamic acid, thionyl chloride, and chlorosulfonic acid. According to Non-Patent Document 2, a bis(fluorosulfonyl)amide potassium salt is obtained by conducting filtration to separate crystals precipitated by adding dropwise methylene chloride into a concentrated solution obtained by separating a reaction liquid obtained by the above-mentioned reaction.

DOCUMENTS OF RELATED ART

Patent Documents

Patent Document 1: Japanese Laid-open Patent Application No. 2006-210331
Patent Document 2: Japanese Translation of PCT International Application Publication No. 2001-527505
Patent Document 3: WO 2011/149095

Non-Patent Documents

Non-patent Document 1: Matsuda Yoshiharu, et al., "Effects of Imide Salt Purity on Negative Electrode Charge-Discharge Characteristics in Lithium Secondary Cells", PROCEEDINGS OF THE 68TH CONFERENCE OF THE ELECTROCHEMICAL SOCIETY OF JAPAN, 25 Mar. 2001, pages 232
Non-patent Document 2: Z. Anorg. Allg. Chem. 2005, 631, 55-59

SUMMARY OF THE INVENTION

Problems to be Solved by the Invention

It is required to provide a di(sulfonylamide) salt in which the content of impurities, such as a solvent that causes deterioration of cell characteristics, is low.

An object of the present invention is to provide granules or powders of a di(sulfonylamide) salt that can meet such a requirement and that are suitable for an electrolyte or the like, and a method for producing the same.

Means to Solve the Problems

The present invention includes the following aspects.
[1] Granules or powders consisting of a compound of formula [I], wherein a modal diameter is 80 μm or less.

[Chemical formula 1]

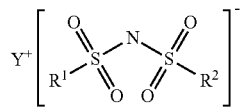

In formula [I], $R^1$ and $R^2$ each independently represents a fluoroalkyl group having 1 to 6 carbon atoms, or a fluorine atom, and $Y^+$ represents an alkali metal cation or an ammonium cation.

[2] The granules or the powders according to [1], wherein the modal diameter is 5 μm to 80 μm.
[3] Granules or powders consisting of a compound of formula [I], wherein a median diameter is 45 μm or less.
[4] The granules or the powders according to [3], wherein the median diameter is 5 μm to 45 μm.
[5] Granules or powders consisting of a compound of formula [I], wherein a ratio of (modal diameter)/(median diameter) is 1.7 or less.
[6] The granules or the powders according to any one of [1] to [5], wherein a concentration of a residual solvent is 1500 ppm or less.
[7] The granules or the powders according to any one of [1] to [5], wherein a concentration of a residual solvent is 800 ppm or less.
[8] The granules or the powders according to any of [1] to [7], wherein $R^1$ and $R^2$ represent fluorine atoms.
[9] An electrolytic solution containing the granules or the powders of any one of [1] to [8] dissolved therein.
[10] A method for producing granules or powders of any one of [1] to [8], including a crystallization step wherein an ester-based solvent solution containing a compound of the formula [I] is added to a halogenated hydrocarbon-based solvent.
[11] The method according to [10], wherein a concentration of the compound of the formula [I] in the ester-based solvent solution is 20% by mass to 90% by mass.

EFFECTS OF THE INVENTION

Granules or powders according to the present invention can be quickly and uniformly dissolved in a solvent, and contribute to increase in efficiency of manufacturing an electrolytic solution available in a secondary cell, a solar cell, or the like. In addition, in the granules or powder according to the present invention, the content of impurities such as solvents, or metal ions, is low, and therefore, it is difficult to cause deterioration of cell characteristics.

EMBODIMENTS FOR CARRYING OUT THE INVENTION

Granules or powders according to the present invention consist of a compound of formula [I].

[Chemical formula 2]

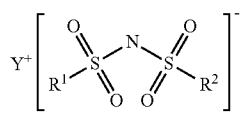

In formula [I], $R^1$ and $R^2$ each independently represents a fluoroalkyl group having 1 to 6 carbon atoms, or a fluorine atom, and $Y^+$ represents an alkali metal cation or an ammonium cation.

Examples of a fluoroalkyl group having 1 to 6 carbon atoms for $R^1$ and $R^2$ include a trifluoromethyl group, a perfluoroethyl group, and a perfluoropropyl group. It is preferable that all hydrogen atoms of an alkyl group in the fluoroalkyl group be substituted with fluorine atoms. Among these, it is preferable that both $R^1$ and $R^2$ be fluorine atoms.

Examples of an alkali metal cation for $Y^+$ include a lithium cation, a sodium cation, and a potassium cation.

The compound of formula [I] may be prepared using a known method. Examples of the method for preparing the compound of formula [I] include: a method in which a sulfamic acid, a thionyl chloride, and a chlorosulfonic acid are reacted, and then the resultant compound is reacted with a potassium fluoride; a method in which a bis(fluorosulfonyl)amine ammonium salt is subjected to a cation exchange reaction in an organic solvent to convert to a bis (fluorosulfonyl)amine lithium sal; and a method in which a bis (chlorosulfonyl)amine ammonium salt is reacted with a hydrogen fluoride.

In an aspect of granules or powders according to the present invention, the modal diameter thereof is preferably 80 μm or less, and more preferably 5 μm to 80 μm. The modal diameter is the particle diameter at the peak of the number-based particle size distribution. The modal diameter in the present invention is determined using a laser diffractometry. Specifically, target granules or powders are dispersed in dichloromethane, and the resultant dispersion is placed on a laser diffraction particle size distribution measurement device (manufactured by Shimazu Corporation, SALD-2200) to conduct a measurement. In the case where the modal diameter is excessively large, the amount of impurities such as a solvent that may cause deterioration of cell properties tends to increase.

In an aspect of granules or powders according to the present invention, the median diameter thereof is preferably 45 μm or less, and more preferably 5 μm to 45 μm. The median diameter is 50% particle diameter in the number-based cumulative particle size distribution. The median diameter in the present invention is determined using a laser diffractometry. Specifically, target granules or powders are dispersed in dichloromethane, and the resultant dispersion is placed on a laser diffraction particle size distribution measurement device (manufactured by Shimazu Corporation, SALD-2200) to conduct a measurement. In the case where the median diameter is excessively large, the amount of impurities such as a solvent that may cause deterioration of cell properties tends to increase.

In an aspect of granules or powders according to the present invention, the ratio of (modal diameter)/(median diameter) thereof is preferably 1.7 or less, and more preferably 1.5 or less. The ratio of (modal diameter)/(median diameter) closer to 1 means that the particle distribution is narrower. The smaller ratio of (modal diameter)/(median diameter) means that there are many fine granules or powders. The modal diameter and the median diameter can be determined using the above-mentioned method. In the case where the ratio of (modal diameter)/(median diameter) increases, it becomes easy to remain impurities such as a solvent without being completely removed from granules or powders in a large particle diameter area.

In a preferable aspect of the granules or powders according to the present invention, the concentration of the residual solvent is preferably 1500 ppm or less, and more preferably 800 ppm or less. The concentration of the residual solvent is the total concentration of the ester-based solvent and the halogenated hydrocarbon-based solvent. In the case where the concentration of the residual solvent is excessively high, the probability of deterioration of the cell properties increases. The concentration of the residual solvent can be determined by analyzing a sample solution using a headspace gas chromatography mass spectrometry system under the following conditions, the sample solution being obtained by adding 50 mg of the target granules or powders to 5 mL of water and 1 μL of methanol and then sealing the resultant.

<Analysis Conditions>

Apparatus: GCMS-QP2010 plus, GC-2010 manufactured by Shimazu Corporation, Turbo Matrix 40 manufactured by PerkinElmer Co., Ltd.

Column: HP-5 (length: 30 m, column inner diameter: 0.53 mm, film thickness: 0.25 μm) (manufactured by Agilent Technologies)

Column temperature condition: 50° C. (held for 0 minute), rising temperature at 5° C./minute up to 100° C. (held for 0 minute)

Headspace condition: vial temperature 70° C. (held for 20 minutes), needle temperature 100° C., transfer line temperature 150° C.

Carrier gas: helium 80 kPa

Interface temperature: 230° C.

Ion source: EI

Ion source temperature: 200° C.

Measurement mode: SIM (target ion m/z 72, confirmation ion m/z 71)

Granules or powders according to the present invention are not particularly limited by the production method thereof. Examples of the production method include: a method containing precipitation or crystallization; a method containing spray-drying; a method containing freeze-drying; a method containing pulverizing, granulating, and/or classifying. Among these, it is preferable to prepare granules or powders by the method containing precipitation or crystallization in the present invention. Although examples of the method containing precipitation or crystallization include an evaporation crystallization method, a cooling crystallization method, and a poor solvent crystallization method, a poor solvent crystallization method is preferable.

Although there are, as a poor solvent crystallization, a method in which a poor solvent is added to a solution and a method in which a solution is added to a poor solvent, the latter method is preferable in the present invention. In the former method, there is a case where conditions for adding a poor solvent (addition rate, addition position, or the like) tend to affect the state of crystallization, which results in, for example, the increased proportion of granules or powders having large particle sizes.

The preferable method for producing the granules or powders according to the present invention includes a crystallization step in which an ester-based solvent solution containing a compound of formula [I] is added to a halogenated hydrocarbon-based solvent.

The ester-based solvent is not particularly limited, provided that the compound of formula [I] exhibits high solubility therein. Examples of the ester-based solvent available in the present invention include an ethyl acetate, a methyl acetate, a butyl acetate, a methoxybutyl acetate, a cellosolve acetate, an amyl acetate, a n-propyl acetate, an isopropyl acetate, a methyl lactate, an ethyl lactate, and a butyl lactate, and an butyl acetate is preferably used.

The ester-based solvent solution containing the compound of formula [I] is obtained by adding and dissolving the compound of formula [I] in the ester-based solvent. Alternatively, the ester-based solvent solution containing the compound of formula [I] is obtained by synthesizing the compound of formula [I] by allowing the above-mentioned reaction to occur in an ester-based solvent. The concentration of the compound of formula [I] in the ester-based solvent solution is preferably 20% by mass to 90% by mass, more preferably 30% by mass to 75% by mass, and even more preferably 30% by mass to 50% by mass. In the case where the concentration is extremely low, the productivity tends to decrease, while in the case where the concentration is extremely high, the viscosity of the solution tends to increase, which is inconvenient.

The halogenated hydrocarbon-based solvent is not particularly limited, provided that the compound of formula [I] exhibits low solubility therein, that is, the halogenated hydrocarbon-based solvent is a poor solvent. Examples of the halogenated hydrocarbon-based solvent available in the present invention include a dichloromethane, a trichloroethylene, a perchloroethylene, a 1, 1-dichloro-1-fluoroethane, a 3, 3-dichloro-1, 1, 1, 2, 2-pentafluoropropane, a 1,3-dichloro-1,1,2,2,3-pentafluoropropane, a bromopropane, and a chloroform, and a dichloromethane is preferably used. Although the amount (volume) of the halogenated hydrocarbon-based solvent to be used is not particularly limited, it is preferably larger than the volume of the ester-based solvent solution.

Conditions for adding the halogenated hydrocarbon-based solvent are not particularly limited. Temperature during crystallization is not particularly limited. For example, crystallization may be conducted at about room temperature, preferably from 0° C. to 50° C.

Then, the granules or powders obtained by crystallization are separated from the mother liquid. As the separation method, a solid-liquid separation operation ordinary in chemical engineering may be adopted. Examples thereof include a precipitation method, and a centrifuge separation method. The separated mother liquid is subjected to liquid-liquid separation to obtain an ester-based solvent and a halogenated hydrocarbon-based solvent, which may be reused in the synthesis step of the compound of formula [I], a crystallization step of the compound of formula [I], or the like. The liquid-liquid separation may be conducted by a known method such as a distillation method.

The granules or powders separated from the mother liquid are dried by a known method. Drying may be conducted by a vacuum drying method, a hot-air drying method, an infrared drying method, a microwave drying method, or the like. Among them, a vacuum drying method is preferable, and a vacuum drying method in which an inert gas is circulated is more preferable. The drying temperature is preferably 20° C. to 70° C., and more preferably 30° C. to 65° C. If the drying temperature is extremely high, there is a case where the decomposition reaction of the compound of the formula [I] occurs. If the drying temperature is extremely low, there is a case where the concentration of the residual solvent increases.

The thus obtained granules or powders according to the present invention are suitable for an electrolyte available in a secondary cell.

An electrolytic solution according to an aspect of the present invention is obtained by dissolving the granules or powders according to the present invention. A solvent to be used in the electrolytic solution may be appropriately selected depending on the intended purpose. Examples of the solvent include an ethylene carbonate, a diethyl carbonate, a dimethyl carbonate, a methylethyl carbonate, a propylene carbonate, a butylene carbonate, a γ-butyrolactone, a vinylene carbonate; imidazolium salt ionic liquids, pyrrolidinium salt ionic liquids, piperidinium salt ionic liquids, pyridinium salt ionic liquid, aliphatic ionic liquids, phosphonium salt ionic liquids, sulfonium salt ionic liquids, ammonium salt ionic liquids, non-aqueous solvents such as iodine-based ionic liquids. An electrolytic solution available in a lithium-ion cell may contain a lithium salt other than the granules or powders according to the present invention. Examples of the lithium salt include $LiClO_4$, $LiPF_6$, $LiAsF_6$, $LiBF_4$, $LiSO_3CF_3$, $CH_3SO_3Li$, and $CF_3SO_3Li$.

EXAMPLES

The present invention is described below in further detail using a series of examples. The present invention is in no way limited by these examples, and can, of course, be practiced with modification as appropriate within a range that can be adaptable to the purposes of the present invention, and those are all encompassed in the technical scope of the present invention.

Synthesis Example 1

Synthesis of di(chlorosulfonyl)amide 123.9 parts by mass of chlorosulfonic acid and 98.1 parts by mass of chlorosulfonyl isocyanate were put in a reaction vessel equipped with a stirrer, a thermometer and a reflux condenser. While stirring the mixture, the temperature thereof was raised to 130° C. over a period of 2.5 hours, then the mixture was reacted for 9 hours at 130° C. Then, the resultant was distilled under reduced pressure to collect a fraction between 98.5° C. and 101° C. at 4.2 torr. 77.9 parts by mass of di(chlorosulfonyl)amide was obtained as a colorless transparent liquid.

Synthesis Example 2

Synthesis of di(fluorosulfonyl) amide ammonium salt 1.07 parts by mass of di (chlorosulfonyl) amide obtained in Synthesis Example 1 was put in a fluorine resin reaction vessel. 7.9 parts by mass of acetonitrile and 0.89 parts by mass of ammonium fluoride were added thereto, and then reacted with refluxing the mixture for 4 hours at 80° C. to 84° C. Then, the resultant was cooled to room temperature, and the insoluble materials were filtered off, and then the resultant was washed with 7.9 parts by mass of acetonitrile. The solvent was then removed under reduced pressure to obtain 0.95 parts by mass of di (fluorosulfonyl) amide ammonium salt.

Example 1

33.4 parts by mass of di(fluorosulfonyl) amide ammonium salt, 69.5 parts by mass butyl acetate, and 102.5 parts by mass of 20% aqueous solution of potassium hydroxide were put in a reaction vessel, and then stirred for 1 hour at 40° C. under a reduced pressure at 100 torr. The reaction mixture was cooled to 25° C. Then, the reaction mixture was separated to obtain an aqueous phase, and then the aqueous phase was extracted twice with 81.1 parts by mass of butyl acetate. The resultant organic phases obtained in the extraction steps were mixed together, and then washed twice with 4.6 parts by mass of water. The solvent in the obtained organic phase was removed under reduced pressure to obtain 91.2 parts by mass of 39.1% by mass of di (fluorosulfonyl) amide potassium salt/butyl acetate solution. The yield was 97%.

91.2 parts by mass of 39.1% by mass of di (fluorosulfonyl) amide potassium salt/butyl acetate solution was added dropwise into 244.1 parts by mass of dichloromethane over a period of 52 minutes at 16 to 24° C. The resultant was cooled to 10° C. over a period of 1 hour. Then, the resultant was stirred at 7 to 10° C. for 42 minutes. The obtained slurry liquid was filtered and washed with 74.0 parts by mass of dichloromethane. The obtained solid was vacuum dried at 6 torr for 13.4 hours at 60° C. to yield 35.1 parts by mass of granules. The yield was 98% with respect to the charged amount of di(fluorosulfonyl)amide potassium salt. The granules had a median diameter of 34.563 μm and a modal diameter of 26.121 μm, and the concentration of the residual solvent therein was 370 ppm (dichloromethane 210 ppm, butyl acetate 160 ppm).

Example 2

71.7 parts by mass of 38.0% by mass of di(fluorosulfonyl) amide potassium salt/butyl acetate solution was obtained in the same manner as that of Example 1.

71.7 parts by mass of 38.0% by mass of di(fluorosulfonyl) amide potassium salt/butyl acetate solution was added dropwise into 167.6 parts by mass of dichloromethane over a period of 30 minutes at 19 to 20° C. The resultant was cooled to 10° C. over a period of 1 hour. Then, the resultant was stirred at 10° C. for 30 minutes. The obtained slurry liquid was filtered and washed with 50.3 parts by mass of dichloromethane. The obtained solid was vacuum dried at 2 torr for 1 hour at 40° C., and then vacuum dried at 0.5 torr for 2 hours at 60° C., to obtain 25.8 parts by mass of granules. The yield was 98% with respect to the charged amount of di(fluorosulfonyl)amide potassium salt. The granules had a median diameter of 35.313 μm, and a modal diameter of 39.619 μm, and the concentration of the residual solvent therein was 640 ppm (dichloromethane 550 ppm, butyl acetate 90 ppm).

Example 3

73.2 parts by mass of 36.5% by mass of di(fluorosulfonyl) amide potassium salt/butyl acetate solution was obtained in the same manner as that of Example 1.

73.2 parts by mass of 36.5% by mass of di(fluorosulfonyl) amide potassium salt/butyl acetate solution was added dropwise into 162.4 parts by mass of dichloromethane over a period of 29 minutes at 24 to 32° C. The resultant was cooled to 12° C. over a period of 2.1 hours. The obtained slurry liquid was filtered and washed with 48.8 parts by mass of dichloromethane. The obtained solid was vacuum dried at 8 to 10° C. for 18.1 hours at 60° C. to obtain 25.3 parts by mass of granules. The yield was 95% with respect to the charged amount of di(fluorosulfonyl)amide potassium salt. The granules had a median diameter of 39.658 μm, and a modal diameter of 39.619 μm, and the concentration of the residual solvent therein was 790 ppm (dichloromethane 430 ppm, butyl acetate 360 ppm).

Example 4

82.0 parts by mass of 37.3% by mass of di(fluorosulfonyl) amide potassium salt/butyl acetate solution was obtained in the same manner as that of Example 1.

82.0 parts by mass of 37.3% by mass of di(fluorosulfonyl) amide potassium salt/butyl acetate solution was added dropwise into 188.1 parts by mass of dichloromethane over a period of 30 minutes at 17 to 19° C. The resultant was cooled to 10° C. over a period of 32 minutes. Then, the resultant was stirred at 5 to 10° C. for 1.2 hours. The obtained slurry liquid was filtered and washed with 56.1 parts by mass of dichloromethane. The obtained solid was vacuum dried at 11 torr for 18.1 hours at 60° C. to obtain 15.5 parts by mass of granules. The yield was 98% with respect to the charged amount of di(fluorosulfonyl)amide potassium salt. The granules had a median diameter of 34.420 μm, and a modal diameter of 39.619 μm, and the concentration of the residual solvent therein was 1160 ppm (dichloromethane 800 ppm, butyl acetate 360 ppm).

Comparative Example 1

81.5 parts by mass of 38.8% by mass of di(fluorosulfonyl) amide potassium salt/butyl acetate solution was obtained in the same manner as that of Example 1.

194.2 parts by mass of dichloromethane was added dropwise into 81.5 parts by mass of 38.8% by mass of di(fluorosulfonyl)amide potassium salt/butyl acetate solution over a period of 39 minutes at 4 to 5° C. After the completion of the addition dropwise, the resultant was stirred at 4 to 5° C. for 1.4 hours. The obtained slurry liquid was filtered and washed with 57.9 parts by mass of dichloromethane. The obtained solid was vacuum dried at 5 torr for 12.3 hours at 60° C., vacuum dried at 4 torr for 20.5 hours at 60° C., and then vacuum dried at 6 torr for 18.9 hours at 60° C., to obtain 30.9 parts by mass of granules. The yield was 98% with respect to the charged amount of di(fluorosulfonyl)imide potassium salt. The granules had a median diameter of 51.796 μm, and a modal diameter of 91.146 μm, and the concentration of the residual solvent therein was 5100 ppm (dichloromethane 2300 ppm, butyl acetate 2800 ppm). The concentration of the residual solvent in the granules having a median diameter larger than 45 μm, a modal diameter larger than 80 μm, and a modal diameter/median diameter ratio larger than 1.7, did not decrease even after a long time drying.

The above results shows that the concentration of the residual solvent is low in granules or powders in which the median diameter is adjusted to 45 μm or less, the modal diameter is adjusted to 80 μm or less, and/or, the ratio of modal diameter/median diameter is adjusted to 1.7 or less, in accordance with the present invention, and therefore the granules or powders are useful as an electrolyte for an electrolytic solution available in a secondary battery, a solar cell, or the like.

INDUSTRIAL APPLICABILITY

Granules or powders according to the present invention can be quickly and uniformly dissolved in a solvent, and contribute to increase in efficiency of manufacturing an electrolytic solution available in a secondary cell, a solar cell, or the like. In addition, in the granules or powder according to the present invention, the content of impurities such as solvents, or metal ions, is low, and therefore, it is difficult to cause deterioration of cell characteristics.

The invention claimed is:

1. Granules or powders consisting of a compound of formula [I],
wherein a modal diameter thereof is 5 μm to 80 μm:

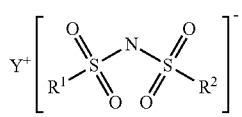

[I]

in the formula [I], $R^1$ and $R^2$ each independently represents a fluoroalkyl group having 1 to 6 carbon atoms, or a fluorine atom, and $Y^+$ represents an alkali metal cation, and
wherein a concentration of a residual solvent is 800 ppm or less.

2. The granules or the powders according to claim 1, wherein $R^1$ and $R^2$ represent fluorine atoms.

3. The granules or the powders according to claim 1, wherein a median diameter is 5 μm to 45 μm and a ratio of (modal diameter) / (median diameter) is 1.7 or less.

4. The granules or the powders according to claim 3, wherein the modal diameter is 5 μm to 39.619 μm.

5. The granules or the powders according to claim 3, wherein the median diameter is 5 μm to 39.658 μm.

6. The granules or the powders according to claim 3, wherein the ratio of (modal diameter) / (median diameter) is 0.76 to 1.15.

7. Granules or powders consisting of a compound of formula [I],
wherein a median diameter thereof is 45 μm or less:

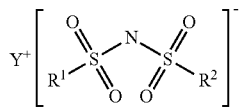

[I]

in the formula [I], $R^1$ and $R^2$ each independently represents a fluoroalkyl group having 1 to 6 carbon atoms, or a fluorine atom, and $Y^+$ represents an alkali metal cation, wherein a concentration of a residual solvent is 800 ppm or less.

8. The granules or the powders according to claim 7, wherein the median diameter is 5 μm to 45 μm.

9. The granules or the powders according to claim 7, wherein $R^1$ and $R^2$ represent fluorine atoms.

10. Granules or powders consisting of a compound of formula [I],
wherein a ratio of (modal diameter)/(median diameter) is 1.7 or less:

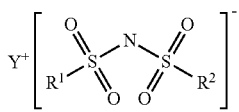

[I]

in the formula [I], $R^1$ and $R^2$ each independently represents a fluoroalkyl group having 1 to 6 carbon atoms, or a fluorine atom, and $Y^+$ represents an alkali metal cation, and
wherein a concentration of a residual solvent is 800 ppm or less.

11. The granules or the powders according to claim 10, wherein $R^1$ and $R^2$ represent fluorine atoms.

12. A method for producing granules or powders of claim 1, comprising
adding an ester-based solvent solution comprising a compound of formula [I] to a halogenated hydrocarbon-based solvent:

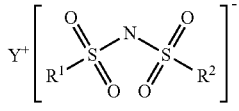

[I]

in the formula [I], $R^1$ and $R^2$ each independently represents a fluoroalkyl group having 1 to 6 carbon atoms, or a fluorine atom, and $Y^+$ represents an alkali metal cation; and
allowing the granules of powders consisting of the compound of formula [I] to crystalize from the ester-based solvent and halogenated hydrocarbon-based solvent,
wherein the modal diameter thereof is 5 μm to 80 μm.

13. The method according to claim 12, wherein a concentration of the compound of the formula [I] in the ester-based solvent solution is 20% by mass to 90% by mass.

* * * * *